United States Patent [19]

Eckstein et al.

[11] 4,331,662

[45] May 25, 1982

[54] METHODS FOR THE TREATMENT OF VIRAL INFECTIONS

[75] Inventors: Fritz Eckstein; John B. Hobbs, both of Göttingen, Fed. Rep. of Germany; Lambert Skoog, Stockholm, Sweden; Gunnar Bjursell, Århus, Denmark; Lars Thelander, Stockholm, Sweden

[73] Assignee: Max-Planck-Gesellschaft zur Forderung der Wissenschaften e.V., Goettingen, Fed. Rep. of Germany

[21] Appl. No.: 118,241

[22] Filed: Feb. 4, 1980

Related U.S. Application Data

[63] Continuation-in-part of Ser. No. 786,323, Apr. 11, 1977, abandoned.

[30] Foreign Application Priority Data

Jun. 16, 1976 [DE] Fed. Rep. of Germany ....... 2627076

[51] Int. Cl.$^3$ ............................................. A61K 31/70
[52] U.S. Cl. .................................................... 424/180
[58] Field of Search ......................................... 424/180

[56] References Cited

U.S. PATENT DOCUMENTS 3,575,959  4/1971  Shen et al. ............................ 536/26

OTHER PUBLICATIONS

Hobbs et al., Biochemistry, 12, No. 25, 1973, pp. 5138–5145.
Chemical Abstracts, 82: 171379c, (1975).
Skoog et al., Eur. J. Biochem., 72, pp. 371–378 (1977)

*Primary Examiner*—Jerome D. Goldberg
*Attorney, Agent, or Firm*—Sprung, Felfe, Horn, Lynch & Kramer

[57] ABSTRACT

Compositions for inhibiting cell growth, particularly compositions for the treatment of virus infections, are provided comprising the nucleoside 2'-azido-2'-desoxycytidine.

1 Claim, 5 Drawing Figures

METHODS FOR THE TREATMENT OF VIRAL INFECTIONS

This is a continuation in part application of Ser. No. 786,323, filed Apr. 11, 1977, now abandoned.

The present invention is concerned with an agent for inhibiting cell growth. More specifically, the invention relates to therapeutic compositions for the treatment of virus infections.

For the duplication of their desoxyribonucleic acid, cells require the constant supply of all four desoxynucleoside triphosphates (desoxyadenosine triphosphate, desoxythymidine triphosphate, dexoycytidine triphosphate and desoxyguanosine triphosphate). In bacterial cells and in mammalian cells, the desoxyribonucleotides are formed by a reduction of the corresponding ribonucleoside diphosphates. This reduction is catalyzed by the enzyme ribonucleotide reductase which consists of two non-identical sub-units, namely, proteins B1 and B2. Protein B1 has active centers for the ribonucleoside diphosphate substrates and for the nucleoside triphosphate effectors (see N. C. Brown and P. Reichard, J. Mol. Biol., 46, 39/1969). Protein B2 contains iron and a free organic radical which are of substantial importance for the activity of the material (see L. Thelander, J. Biol. Chem., 248, 4591/1973); C. L. Atkin, L. Thelander, P. Reichard and G. Lang, J. Biol. Chem., 248 7464/1973).

Since ribonucleotide reductase is an essential substance in the metabolic cycle which leads to the synthesis of desoxyribonucleic acid, it is obvious that impairment of the activity of this enzyme results in an inhibition of the desoxyribonucleic acid synthesis in the cell. Hitherto, only one substance has become known, namely hydroxyurea, which inhibits the activity of ribonucleotide reductase not only in vitro but also in vivo (see I. H. Krakoff, N. C. Brown and P. Reichard, Cancer res., 28, 1559/1968; L. Skoog and B. Nordenskjöld, Eur. J. Biochem., 19, 81/1971). Interesting results have been achieved with this compound not only with regard to the nucleotide metabolism but also with regard to the duplication of desoxyribonucleic acid (see L. Skoog and B. Nordenskjöld, loc. cit.; G. Magnusson, R. Craig, M. Närkhammar, P. Reichard, M. Staub and H. Warner, Cold Spring Harbor Symp. on Quant. Biology, 29, 227/1975). However, hydroxyurea is a very reactive compound and its specificity for the in vivo inhibition of ribonucleotide reductase has already been doubted (see H.S. Rosenkranz, S. Jacobs and H. Carr, Biochimica et Biophysica Acta, 161, 428/1968).

It has already been found (see L. Thelander, B. Larsson, J. Hobbs, F. Eckstein, J. Biol. Chem., 251, 1398-1405/1976) that certain nucloside diphosphates which have an azido group in the 2'-position of the ribose residue react in vitro with ribonucleoside diphosphate reductase and lead to a complete loss of the enzymatic activity of this material.

We have now, surprisingly, found that, as nucleosides, 2'-azido-2'-desoxycytidine, 2'-azido-2'-desoxyadenosine and 2'-azido-2'-desoxyguanosine inhibit the desoxyribonucleic acid synthesis of living cells. This inhibition is not due to an inhibition of the reductase but occurs via a new mechanism. Because of their specificity, they are excellent inhibitors of the desoxynucleic acid synthesis of the living cell. Cell growth is hereby impaired so that it is possible to use these compounds for the therapeutic treatment of virus infections.

Therefore, according to the present invention, there is provided a composition for the inhibition of cell growth, which comprises at least one of 2'-azido-2'-desoxyadenosine, 2'-azido-2'-desoxyguanosine and 2'-azido-2'-desoxycytidine as the active agent, together with a conventional pharmaceutical binding agent, carrier material and/or adjuvant material.

2'-azido-2'-desoxycytidine can be prepared by the methods hereinafter described and 2'-azido-2'-desoxyadenosine and 2'-azido-2'-desoxyguanosine can be prepared from 2'-azido-2'-desoxyuridine by the process which is described in German patent application P No. 26 28 202.0, filed simultaneously with the German priority application of the instant case.

In the following examples, which are given for the purpose of illustrating the present invention, reference is made to the accompanying drawings, in which.

EXAMPLE 1

Preparation of 2'-azido-2'-desoxyuridine

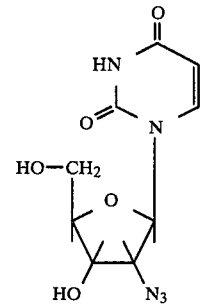

Figure 1:
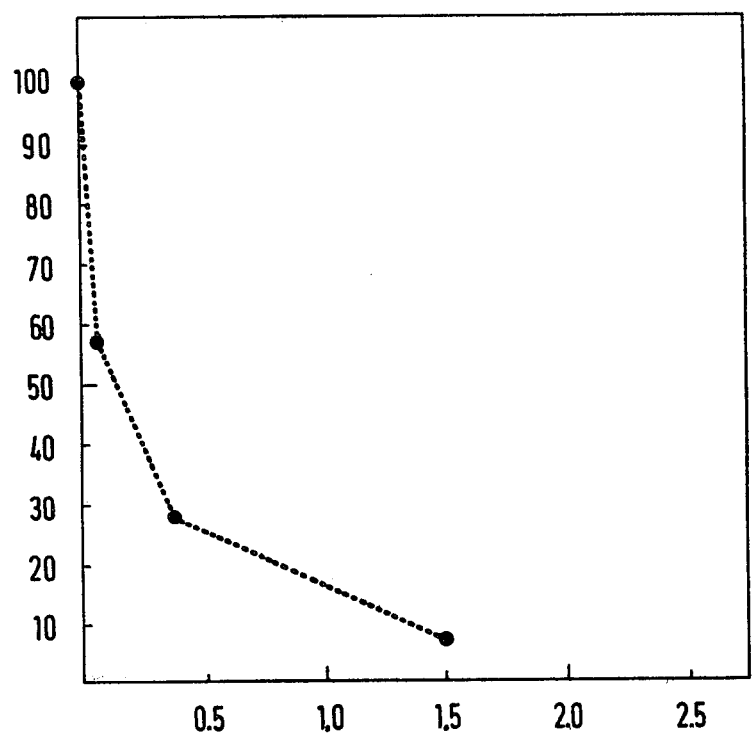
FIG. 1 is a graph plotting the action of 2'-azido-2'-desoxycytidine according to the present invention on the rate of desoxyribose-nucleoic acid synthesis.

10 g. uridine were stirred with 12 g. diphenyl carbonate in 80 ml. hexamethyl phosphoric acid triamide on an oil bath at a temperature of 140° C., thereafter 0.24 g. sodium bicarbonate was added thereto. When gas evolution ceased (after about 30 minutes), 8 g. lithium azide was added to the reaction mixture. After heating for about 2 hours, the thin layer chromatogram shows, in solvent system A (methanol/chloroform mixture (¼ v/v)), that the $O^2,2'$-cyclouridine had almost completely disappeared. The solution was then cooled, diluted with 160 ml. water and extracted twice with 160 ml. amounts of water. The combined aqueous solutions were then again extracted three times with 200 ml. amounts of chloroform. The aqueous solutions were evaporated in a vacuum and the residue was thoroughly stirred with a mixture of 160 ml. acetone and 60 ml. methanol and filtered. The filtrate was evaporated and the remaining oil was chromatographed on 700 g. silica gel which has been equilibrated with acetone, using acetone as elution agent. The fractions containing the desired product were applied to 6 plates coated with silica gel (2 mm. layer thickness, 20×40 cm.) for preparative thin layer chromatography, the plates being developed with an acetone/ethyl acetate mixture (1/1 v/v). The regions containing the product were scraped off and eluted with acetone. The acetone solution was evaporated and the residue was taken up with 45 ml. pyridine and filtered in order to remove traces of silica gel. The pyridine was then evaporated and traces of pyridine were removed by the addition of water and evaporation of the water. The product thus obtained is a viscous yellow oil which proved to be thin layer chromatographically pure (in the solvent system A and an acetone/ethyl acetate mixture (1/1 v/v)). The product is obtained in a yield of 5.49 g. (50% of theory). This compound can also be used for the preparation of 2'-azido-2'-desoxycytidine. When left to stand at ambient temperature, the oil crystallizes out spontaneously.

For analysis, the product was applied to an ion exchanger column ("Dowex" 1×4) (OH), whereupon the column was washed with water and then with 50% aqueous methanol and subsequently eluted with a 0.1 M triethyl ammonium carbonate solution. The solution was evaporated, methanol was added to the residue and the solution was again evaporated. The residue was stirred with acetone, the acetone was evaporated and the residue applied to a small column filled with silica gel which was then eluted with acetone. The acetone solution was evaporated and the residue crystallizes, upon scratching, to give white needles which melt, with a grey coloration and with decomposition, at 139° to 147° C., the decomposition taking place very quickly above 180° C.

Analysis:
$C_9H_{11}N_5O_5$ 
calc.: C:40.15%; H:4.09%; N:26.02%; found: C:40.51%; H:3.80%; N:26.15%.

UV spectrum: $\lambda_{max} = 260$ nm ($\epsilon = 9.3 \times 10^3$).

The IR spectrum and the NMR spectrum are identical with those given in the literature for 2'-azido-2'-desoxyuridine (see J. P. H. Verheyden, D. Wagner and J. G. Moffatt, J. Org. Chem. 36, 250/1971).

EXAMPLE 2

2'-Azido-2'-desoxycytidine

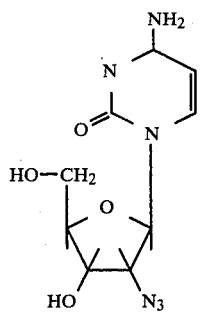

1 g. 2'-Azido-2'-desoxy-3',5'-diacetyl-uridine (see J. Hobbs, H. Sternbach, M. Sprinzl and F. Eckstein, Biochemistry, 12, 5138/1973) was mixed with 14 ml. ethanol-free chloroform and 0.14 ml. dimethyl formamide and then mixed with 2 ml. thionyl chloride. The reaction mixture was boiled under reflux, with the exclusion of moisture, for 6 hours. After cooling, the reaction mixture was evaporated in a vacuum and the residue treated with ammoniacal methanol (30 ml. dry methanol plus 30 ml. methanol saturated with ammonia). The solution was stirred for 2 days at ambient temperature and then left to stand for 2 days at 37° C. Thin layer chromatography (methanol/chloroform mixture (4/6 v/v) on silica gel plates, Herck 60 F 254) shows mainly a product with an $R_f$ value of 0.62. The solution was evaporated, the residue applied to two plates coated with silica gel for preparative thin layer chromatography (Merck 60 F 254, 2 mm. layer thickness, 20×40 cm.) and developed with a chloroform/methanol mixture (6/4 v/v). The main bands were scraped off, the material was eluted with methanol and applied to an ion exchanger column (Dowex 1×2, OH, 1.7×21.5 cm.). After washing with water, the product was eluted with 30% aqueous methanol. The solution obtained was evaporated and the residue recrystallized from ethanol. 2'-Azido-2'-desoxycytidine was obtained in a yield of 12310 $A_{270}$ units (1.32 mMol; 47% of theory). The product melts at 215° C.

EXAMPLE 3

Pharmacological investigations.

Ovarian cells of the Chinese hamster were cultivated in Eagle's medium with 10% fetal calf serum. The cells were incubated at 37° C., in air containing 4% carbon dioxide. To the logarithmically growing cells was added, over the course of 2 hours, 2'-azido-2'-desoxycytidine in various concentrations. After expiry of this time, the [³H]-thymidine incorporation into material precipitable with acid was measured over 30 minute intervals (see L. Skoog and B. Nordenskjöld, loc. cit.). Both substances inhibit the synthesis of desoxyribonucleic acid to the same extent. At a concentration of 2.5 mMol per liter, the synthesis was only 10% of that of the untreated control cells.

This effect is illustrated by the curve shown in FIG. 1 in which the concentration of the active material in the culture cultured in the presence of 2'-azido-2'-desoxycytidine (●) is plotted against the percentage [³H]-thymidine incorporation.

Figure 2:
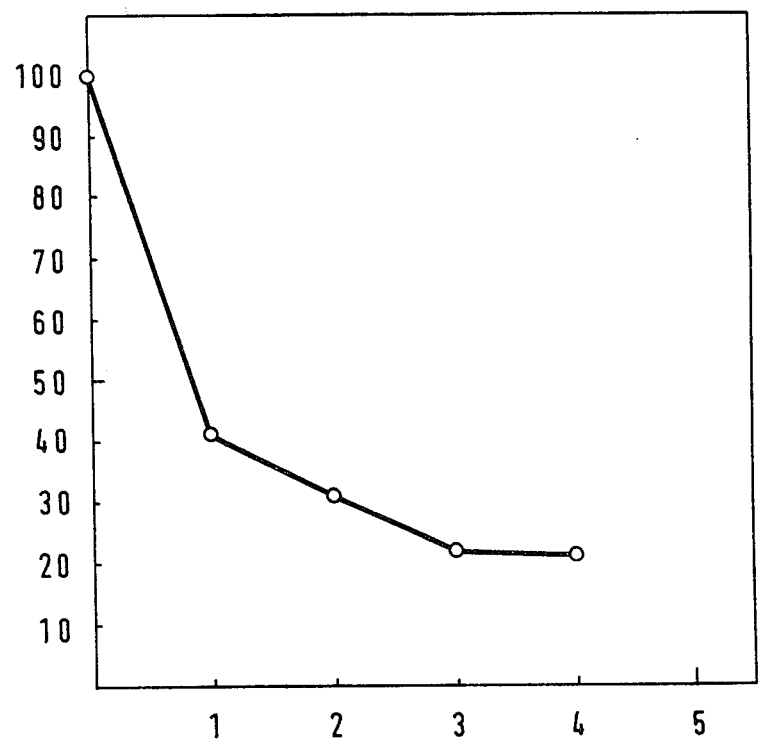
FIG. 2 is plot showing the dependence of inhibition on the time.

The maximum inhibition of the desocyribonucleic acid synthesis is observed 3 to 4 hours after the addition of 2'-azido-2'-desoxycytidine in a concentration of 1.3 mMol per liter. This can be seen from FIG. 2 in which the percentage incorporation of [³H]-thymidine is plotted against the time in hours after the addition of the active material.

Figure 3:
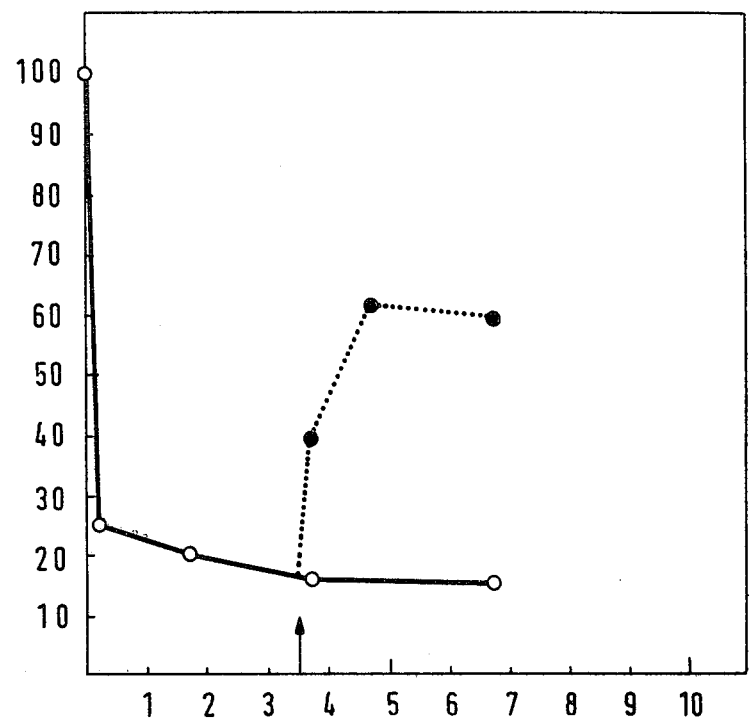
FIG. 3 is a plot showing the action of 2'-azido-2'-desoxycytidine on the synthesis of desoxyribonucleic acid.

When the active material 2'-azido-2'-desoxycytidine is again removed after a period of action of 3.5 hours, the [³H]-thymidine incorporation again increases. This effect can be seen from FIG. 3. The plotted curve is obtained by adding 2'-azido-2'-desoxycytidine initially at a concentration of 1.6 mMol per liter to logarithmically growing ovarian cells of the Chinese hamster. The cells are subjected to the action of the active material for 3.5 hours, thereafter the active material is removed by rinsing well and incubation is continued with fresh medium. The rate of synthesis of desoxyribonucleic acid is then measured in the given intervals by the rate of incorporation of [³H]-thymidine. The curve indicated with (o) concerns the cells incubated with the active material, whereas the curve (●) indicates the rinsed cell cultures.

Figure 4:
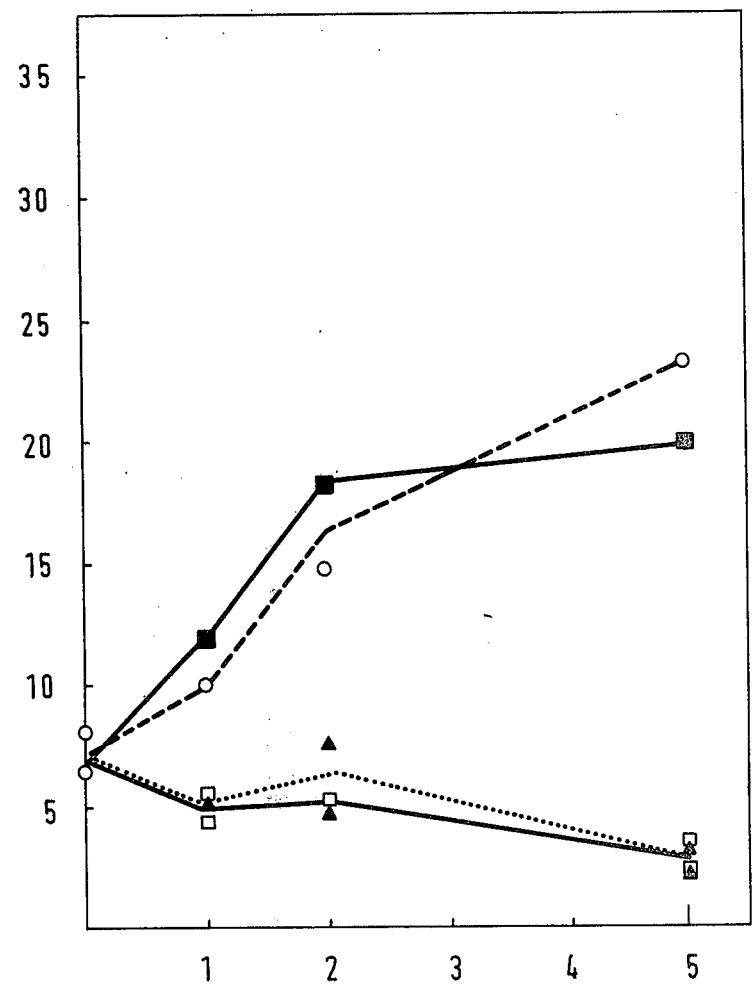
FIG. 4 is a plot showing the action of 2'-azido-2'-desoxycytidine on the cell growth.

In the same investigation, we found that cells grow normally at a concentration of 2'-azido-2'-desoxycytidine of 20 μmol per liter, whereas cell growth is completely blocked when the concentration of the active material is 0.2 mMol per liter or 2 mMol per liter. After treatment for five days at this high concentration, the desoxyribonucleic acid content of the cells decreases to 50%, which corresponds to a progressive cell death. These results can be seen from FIG. 4 in which there is plotted the desoxyribonucleic acid content in μg. against the number of days of treatment. The curve indicated with (o) corresponds to the cultures grown without the active material, the curve (■) indicates the cultures incubated in the presence of 20 μMol per liter 2'-azido-2'-desoxycytidine, the curve (▲) indicates the cultures incubated in the presence of 0.2 mMol per liter of this active material and the curve (□) indicates the growth of the cells in the presence of 2 mMol per liter of this active material.

Figure 5:
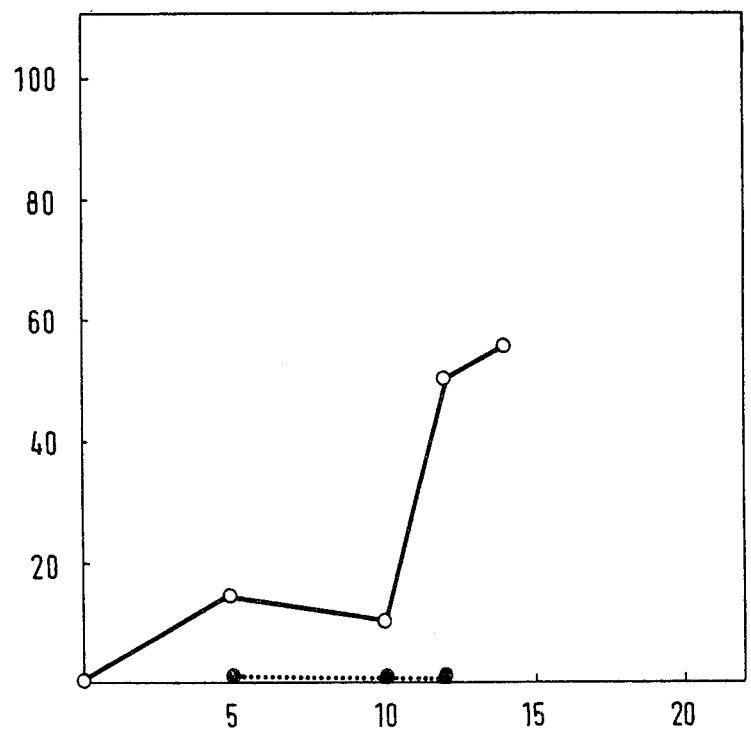
FIG. 5 is a plot showing the influence of 2'-azido-2'-desoxycytidine on the desoxyribonucleic acid synthesis of synchronized ovarian cells of the Chinese hamster.

In a further investigation, ovarian cells of the Chinese hamster are synchronized by the withdrawal of isoleucine for 48 hours. The complete medium is then added thereto, followed by autoradiographic determination of the proportion of cells participating in the synthesis of desoxyribonucleic acid. The results obtained are given in FIg. 5 in the form of curves obtained by plotting the percentage of radioactively-marked cells against the time after stimulation. The curve indicated with (o) stands for the stimulated cultures, whereas the curve indicated with (●) stands for the cell cultures which, simultaneously with the changes of the medium, received 1.5 mMol per liter 2'-azido-2'-desoxycytidine. It can be seen that the number of radioactively-marked cells has increased from 0.3 to 10% 5 hours after stimulation. In the course of 14 hours after the change of the culture medium, this value increases to 55%. Furthermore, it can be seen that the addition of the active material completely blocks the desoxyribonucleic acid synthesis in the stimulated cultures.

An analysis of the cultures for their content of nucleoside triphosphates shows that the desoxyribonucleic acid-synthesizing cells contain 5.2, 3.7, 1.0 and 7.1 pMol/μg., respectively, of desoxyribonucleic acid from desoxyadenosine triphosphate, desoxycytidine triphosphate, desoxyguanosine triphosphate and desoxythymidine triphosphate, respectively. The simultaneous addition of 2'-azido-2'-desoxycytidine with the changed medium leads to increased amounts of desoxyadenosine triphosphate and desoxythymidine triphosphate, whereas, on the other hand, the content of desoxycytidine triphosphate and desoxyguanosine triphosphate has decreased by 60 and 30%, respectively.

From the above results, it can be seen that 2'-azido-2'-desoxycytidine blocks cell growth by inhibition of the desoxyribonucleic acid synthesis.

Neither desoxycytidine nor cytidine can protect the cells or remove the action of 2'-azido-2'-desoxycytidine. This can be seen from the following Table I:

TABLE I

Action of cytosine nucleosides on the inhibition of the desoxyribonucleic acid synthesis by 1 mMol per liter 2'-azido-2'-desoxycytidine. The rate of desoxyribonucleic acid synthesis is thereby determined by the incorporation of [$^3$H]-thymidine into an acid-insoluble product 4.5 hours after the addition of the active material. The end concentration of the cytosine nucleosides is 1 mMol per liter.

| active material | [$^3$H]-thymidine incorporation cpm/μg. DNS |
| --- | --- |
| control | 9186 |
| 2'-azido-2'-desoxycytidine (azido C) | 230 |
| azido-C + desoxycytidine (added simultaneously) | 224 |
| azido C + desoxycytidine (added 4.5 hours later) | 299 |
| azido-C + cytidine (added simultaneously) | 286 |
| azido-C + cytidine (added 4.5 hours later) | 278 |

It can be seen that desoxycytidine cannot remove the inhibition even in the case of simultaneous addition of the active material 2'-azido-2'-desoxycytidine. 2'-Azido-2'-desoxycytidine possesses, in synchronized cells, little effect upon the amount of intracellular desoxynucleoside triphosphates. This is to be seen from the following Table II:

TABLE II

Action of 2'-azido-2'-desoxycytidine on the amount of intracellular desoxynucleoside triphosphates (the active material is added 14 hours after stimulation, whereupon the rate of desoxyribonucleic acid synthesis is measured in 5 minute intervals with regard to the [$^3$H]-thymidine incorporation).

| time after the addition of 2'-azido-2'-desoxycytidine | [$^3$H]-thymidine incorporation (cpm/μg. DNS) | intracellular amounts of desoxynucleoside triphosphates (pMol/μg. DNS) | | | |
| --- | --- | --- | --- | --- | --- |
| | | dATP | dCTP | dGTP | dTTP |
| 30 minutes | 92 | 5.7 | 3.1 | 0.9 | 5.4 |
| 90 minutes | 45 | 7.5 | 1.9 | 1.1 | 9.1 |
| control cells | 285 | 5.2 | 3.7 | 1.0 | 7.1 | dATP = desoxyadenosine triphosphate
dCTP = desoxycytidine triphosphate
dGTP = desoxyguanosine triphosphate
dTTP = desoxythymidine triphosphate The synthesis of polyoma desoxyribonucleic acid in 3T6 cells infected with polyoma viruses is also, by the addition of 2'-azido-2'-desoxycytidine ($3 \times 10^{-3}$) mol per liter) 24 hours after the infection, 90% inhibited after 20 or 40 minutes incubation time. The sedimentation profile of the desoxyribonucleic acid from the control cells and the cells treated with the active material show the same profile.

It can be seen that the active materials used according to the present invention inhibit the synthesis of desoxyribonucleic acid in mammalian cells and that, therefore, they are active materials against the duplication of desoxyribonucleic acid and thus against cell growth. As investigations show, the rate of chain lengthening in the case of duplication of the desoxyribonucleic acid molecules is not influenced but clearly a blocking of the desoxyribonucleic acid synthesis takes place by a specific inhibition of an important function at an early stage of the desoxyribonucleic acid duplication.

The active materials according to the present invention can be employed with the use of conventional pharmaceutical techniques to give medicinal preparations of conventional formulation, for which purpose there are used pharmaceutically compatible binding agents, carrier materials and/or adjuvant materials.

The active materials can also be mixed with other active materials which do not inpair the desired action and/or supplement the desired action.

The active materials according to the present invention can be administered orally or parenterally in liquid or solid form. For injection purposes, the medium used must, of course, be a sterile liquid. As injection medium, it is preferred to use water which contains the stabilizing agents, solubilizing agents and/or buffers conventional in the case of injection solutions. Additives of this type include, for example, tartrate and borate buffers, ethanol, dimethyl sulphoxide, complex-forming agents (for example ethylenediamine-tetraacetic acid), high molecular weight polymers (for example liquid polyethylene oxide) for viscosity regulation or polyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats or solid high molecular weight polymers (such as polyethylene glycols). Compositions suitable for oral administration can, if desired, contain flavoring and/or sweetening agents.

The active materials according to the present invention can be employed in dosages and amounts which are conventional in the art. Thus, the materials can be applied at a dosage of at least 20 to 200 mg/kg, depending of the specific virus being treated and use of amounts as high 1,000 to 2,000 mg/kg may be indicated.

It will be understood that the specification and examples are illustrative, but not limitative of the present invention and that other embodiments within the spirit and scope of the invention will suggest themselves to those skilled in the art.

What is claimed is:

1. A method for the treatment of virus infections by inhibition of DNA synthesis comprising administering to an afflicted subject in an amount effective in the treatment of virus infection by inhibition of DNA synthesis of 2'-azido-2'-desoxycytidine.

* * * * *